United States Patent [19]

Ogiu

[11] Patent Number: 4,890,159
[45] Date of Patent: Dec. 26, 1989

[54] ENDOSCOPE SYSTEM AND METHOD OF UNIFYING PICTURE IMAGES IN AN ENDOSCOPE SYSTEM

[75] Inventor: Hisao Ogiu, Hachioji, Japan

[73] Assignee: Olympus Optical Co., Ltd., Tokyo, Japan

[21] Appl. No.: 283,826

[22] Filed: Dec. 13, 1988

[30] Foreign Application Priority Data

Feb. 4, 1988 [JP] Japan .................................. 63-25446

[51] Int. Cl.⁴ ........................... A61B 1/04; H04N 7/18
[52] U.S. Cl. ....................................... 358/98; 358/160; 128/6
[58] Field of Search ..................... 358/98, 22, 160, 93; 382/46; 128/4, 6

[56] References Cited

U.S. PATENT DOCUMENTS

| 4,601,284 | 7/1986 | Arakawa et al. | 358/98 X |
| 4,677,470 | 6/1987 | Cooper et al. | 358/160 X |
| 4,755,873 | 7/1988 | Kobayashi | 358/98 |
| 4,774,568 | 9/1988 | Matsuo | 358/98 |

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

This endoscope system comprises a plurality of types kind of endoscope apparatuses, a signal processing apparatus used in common with the plurality of types of endoscope apparatuses and which processes the output signal of the imaging apparatus of each endoscope apparatus to be a video signal and an apparatus for unifying the picture image in the signal output from the plurality of kinds of endoscope apparatus to be a right image or a mirror image and inputs the unified signal into the signal processing apparatus. The plurality of types of endoscope apparatuses have each an elongate insertable part, an image forming optical system provided in the tip part of the insertable part and an imaging apparatus imaging the object image formed by the image forming optical system. At least one endoscope is different from the other endoscopes in whether the image formed by the image forming optical system is a right image or a mirror image. A method of unifying the picture image in the signal output from the signal processing apparatus to be a right image or a mirror image includes unifying the picture image in the signal output from the endoscope apparatus into a right image or a mirror image before it is input into the signal processing apparatus.

21 Claims, 12 Drawing Sheets

ENDOSCOPE SYSTEM AND METHOD OF UNIFYING PICTURE IMAGES IN AN ENDOSCOPE SYSTEM

BACKGROUND OF THE INVENTION:

1. Field of the Invention

This invention relates to an endoscope system wherein a common signal processing apparatus can be used for a plurality of types of endoscope apparatuses without inverting images.

2. Related Art Statement

Recently, there is extensively utilized an endoscope whereby organs within a body cavity can be observed by inserting an elongate insertable part into the body cavity or various curing treatments can be made by using treating tools inserted through a treating tool channel as required.

Also, there are suggested various electronic endoscopes using a solid state imaging device such as a charge coupled device (CCD).

Now, there has been a problem that, in the above mentioned electronic endoscopes such as, for example, between a straight viewing endoscope and a side viewing endoscope, the objective optical system is different and therefore, in case the same signal processing is applied, the image of either of the straight viewing endoscope and side viewing endoscope will be inverted. This problem will occur not only in the case of the straight viewing and side viewing but also when the arrangement of this solid state imaging device is changed, for example, by the size of the solid state imaging device or the like.

In order to cope with it, in the publication of a Japanese patent application laid open No. 211040/1987, there is disclosed an endoscope apparatus wherein, so that a common video processing apparatus may be used, an endoscope is provided with a recording means for discriminating the type of endoscope, a signal set in this recording means is discriminated by a discriminating circuit provided in the video processing apparatus and, for the endoscope in which the observed image becomes a mirror image (called also a back image), the image is passed through an image inverting circuit so as to be corrected to a right image.

However, in this related art example, it is necessary to provide an endoscope with a recording means for discriminating the kind of the endoscope and is costly.

Also, it is necessary to incorporate into the video processing circuit an image inverting circuit, endoscope discriminating circuit and switching circuit switching the circuit in response to the type of endoscope and has been a cause of enlarging the video processing apparatus and elevating the cost.

In a U.S. Pat. No. 4,369,459, there is dosclosed a technique wherein an image inverted by an optical member is made a right image by reversing the direction of reading out the solid state imaging device from the normal direction.

However, this prior art is to determine the state of an image in one television camera but does not disclose a means of enabling a plurality of type of endoscopes to be used in a common signal processing apparatus.

OBJECT AND SUMMARY OF THE INVENTION:

An object of the present invention is to provide an endoscope system whereby a common signal processing apparatus can be used for a plurality of types of endoscope apparatus with a simple formation without inverting the image.

Another object of the present invention is to provide an endoscope system whereby a common signal processing apparatus can be used for a plurality of types of endoscope apparatus with a simple formation without inverting the image and changing the position of the rotating direction of the image.

Further another object of the present invention is to provide a method of unifying picture images in an endoscope system whereby a common signal processing apparatus can be used for a plurality of types of endoscope apparatus with a simple formation without inverting the image.

An endoscope system of the present invention comprises a plurality of types of endoscope apparatuses having an imaging device, a signal processing apparatus used in common for the above mentioned plurality of types of endoscope apparatuses and processing the output signals of the imaging device of the respective endoscope apparatuses to be video signals without making different processes in response to the types of the endoscope apparatuses with respect to the invension of the right images and mirror images of the picture images and an apparatuses for unifying to right images or mirror images the picture images in the signals output from the above mentioned plurality of types of endoscope apparatuses and input into the above mentioned signal processing apparatus. The above mentioned plurality of types of endoscope apparatuses have each an elongated insertable part, an image forming optical system provided in the tip part of the above mentioned insertable part and an imaging device imaging the object image formed by the above mentioned image forming optical system. At least one type is different from any other types in respect that the image formed by the above mentioned image forming optical system is a right image or a mirror image. The endoscope system is further provided with an apparatus for unifying in all the endoscope apparatuses the positions of the rotating directions of the picture images in the output signals of the above mentioned imaging device. In the endoscope system whereby a common signal processing apparatus can be used for a plurality of types of endoscope apparatuses without inverting the image, the method of unifying the picture images in the signals output from the above mentioned signal processing apparatus to be right images or mirror images includes unifying the picture images in the signals input into this signal processing apparatus to be right images or mirror images before they are input into the above mentioned signal processing apparatus.

The other features and advantages of the present invention will become apparent enough with the following explanation.

BRIEF DESCRIPTION OF THE DRAWINGS:

FIG. 1 is a sectioned view of the tip part of an insertable part of a straight viewing endoscope using a small solid state imaging device.

FIG. 2 is an arrangement explaining view as seen from the tip side of a cross-section including the solid state imaging device of the endoscope in FIG. 1.

FIG. 3 is an explanatory view showing a monitor displayed picture image of the endoscope in FIG. 1.

FIG. 4 is an arrangement explaining view as seen from the tip side of a cross-section including the solid state imaging device of a straight viewing endoscope using a smaller solid state imaging device.

FIG. 5 is a sectioned view of the tip part of an insertable part of a straight viewing endoscope using a large solid state imaging device.

FIG. 6 is an explanatory view showing the solid state imaging device of the endoscope in FIG. 5.

FIG. 7 is an explanatory view showing a monitor displayed picture image of the endoscope in FIG. 5.

FIG. 8 is an explanatory view showing a horizontal transferring part of the solid state imaging device of the endoscope in FIG. 1.

FIG. 9 is an explanatory view showing a horizontal transferring part of the solid state imaging device of the endoscope in FIG. 5.

FIG. 10 is a sectioned view of the tip part of an insertable part of a side viewing endoscope using a small solid state imaging device.

FIG. 11 is an explanatory view showing a solid state imaging device of the endoscope in FIG. 10.

FIG. 12 is an explanatory view showing a monitor displayed picture image of the endoscope in FIG. 10.

FIG. 13 is a sectioned view of the tip part of an insertable part of a side viewing endoscope using a large solid state imaging device.

FIG. 14 is an explanatory view showing an image forming optical system of the endoscope in FIG. 13.

FIG. 15 is an explanatory view showing a solid state imaging device of the endoscope in FIG. 13.

FIG. 16 is an explanatory view showing a monitor displayed picture image of the endoscope in FIG. 13.

FIG. 17 is a perspective view showing the entirety of an electronic endoscope system.

FIG. 18 is a block diagram showing the formation of an electronic endoscope system.

FIG. 23 is a perspective view showing the entirety of an endoscope system.

FIG. 24 is an explanatory view showing the scheme of a fiber scope and video converter.

DETAILED DESCRIPTION OF THE PREFERRED EMBODIMENTS:

The first embodiment of the present invention is shown in FIGS. 1 to 18.

Figure 17:
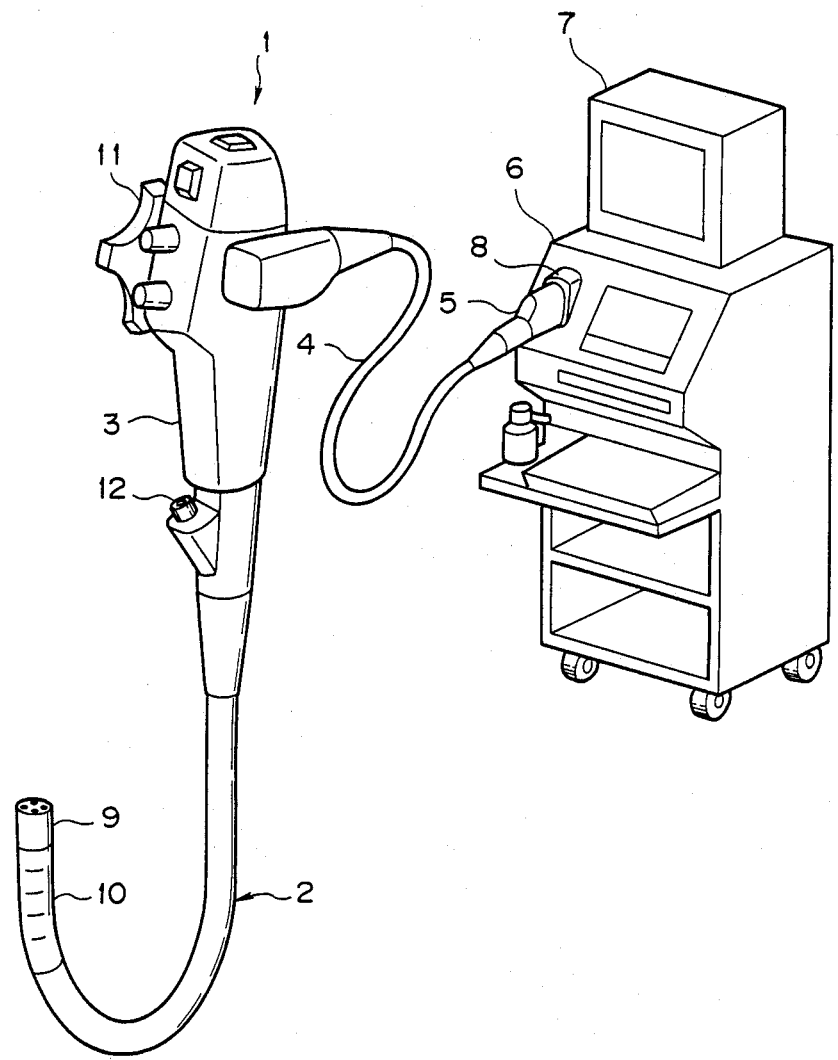

As shown in FIG. 17, an electronic endoscope system comprises an electronic endoscope 1, a video processor 6 containing a light source apparatus and signal processing circuit and connected with the above mentioned electronic endoscope 1 and a monitor 7 connected to this video processor 6.

The above mentioned electronic endoscope 1 is provided with an elongate and, for example, flexible insertable part 2 and a thick operating part 3 connected to this insertable part 2 at the rear end. A flexible universal cord 4 is extended sidewise from the above mentioned operating part 3 and is provided at the tip with a connector 5 to be connected to a connector receptacle 8 of the above mentioned video processor 6.

A rigid tip part 9 and a curvable part 10 curvable rearward and adjacent to this tip part 9 are provided in turn on the tip side. The above mentioned operating part 3 is provided with a curving operation knob 11 so that the above mentioned curvable part 10 may be curved vertically and horizontally by rotating and operating this curving operation knob 11. Further, the above mentioned operating part 3 is provided with a treating tool inserting port 12 communicating with a treating tool channel provided through the above mentioned insertable part 2.

Figure 18:
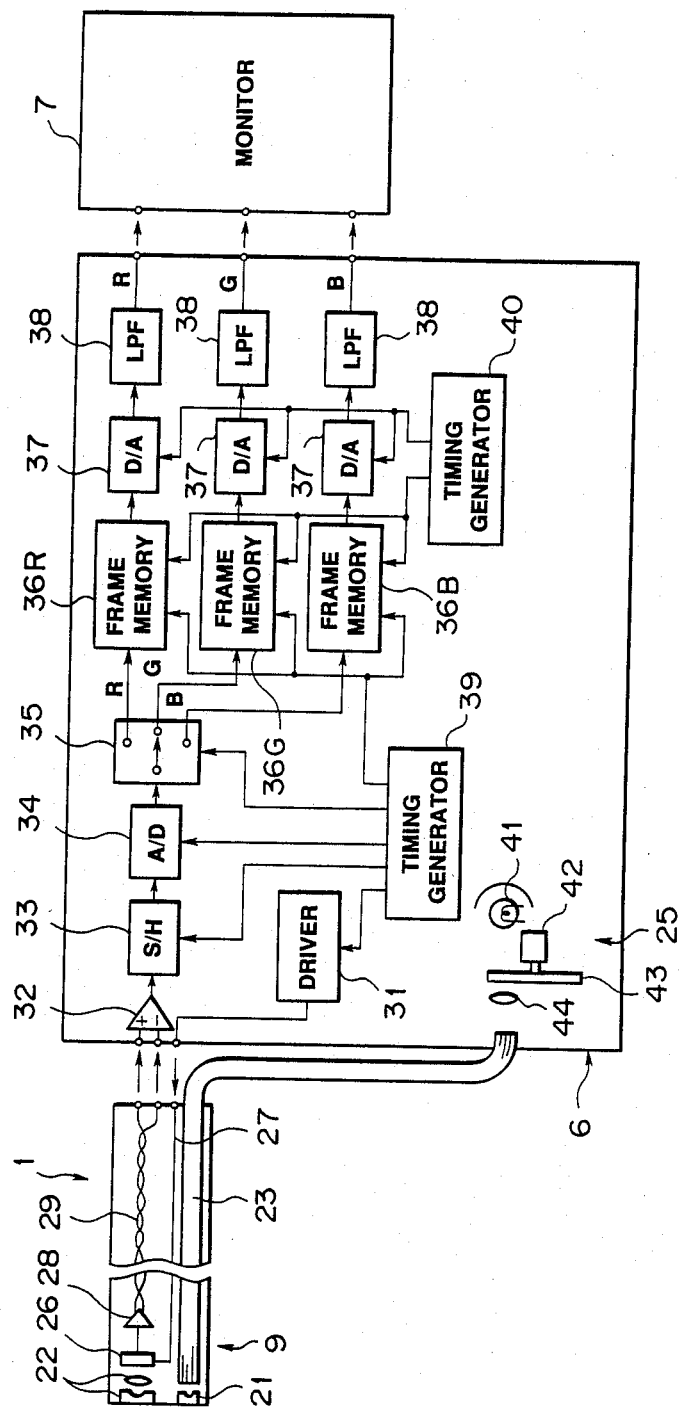

As shown in FIG. 18, a light distributing lens 21 and an image forming optical system 22 are arranged in the above mentioned tip part 9. A light guide 23 made of a fiber bundle is connected to the above mentioned light distributing lens 21 on the rear end side, is inserted through the above mentioned insertable part 2, operating part 3 and universal cord 4 and is connected to the above mentioned connector 5 so that, when this connector 5 is connected to the above mentioned video processor 6, the illuminating light emitted from the light source apparatus 25 within this video processor 6 will enter the above mentioned light guide 23 at the entrance end, will be led to the tip part 9 by the above mentioned light guide 23, will be emitted from the tip surface, will pass through the light distributing lens 21 and will be radiated to an object to be imaged.

In this embodiment, a field sequential type is used as a color imaging system. The above mentioned light source apparatus 25 has a lamp 41 emitting a white color light. The light emitted from this lamp 41 passes through a rotary filter 43 in which filters respectively transmitting the light of respective wavelength regions of red(R), green(G) and blue(B) are arranged in the peripheral direction and which is rotated and driven by a motor 42, is separated into the light of R, G and B in time series, is condensed by a condenser lens 44 and enters the above mentioned light guide 23 at the entrance end.

On the other hand, a solid state imaging device 26 is arranged in the image forming position of the above mentioned image forming optical system 22. A signal line 27 for driving pulses and a signal line 29 for output signals through a pre-amplifier 28 using a differential amplifier are connected to the above mentioned solid state imaging device 26. These signal lines 27 and 29 are inserted through the above mentioned insertable part 2, operating part 3 and universal cord 4 and are connected to the above mentioned connector 5. The signal line 27 for driving pulses is connected to a driver 31 provided within the above mentioned video processor 6. On the other hand, the signal line 29 for output signals is connected to a differential amplifier 32 provided within the above mentioned video processor 6.

The output signal of the solid state imaging device 26 driven and read out by the driving pulses from the above mentioned driver 31 is input into the pre-amplifier 28, the reversed output and non-reversed output of this pre-amplifier 28 are input into the differential amplifier 32 through the above mentioned signal line 29 and a pixel signal is output from this differential amplifier 32. The output signal of the above mentioned differential amplifier 32 is sample-held in a sample holding circuit 33, is converted to a digital signal by an A/D converter 34 and is stored in frame memories 36R, 36G and 36B corresponding to the respective colors of R, G and B through a multiplexer 35. The respective timings of the above mentioned sample holding circuit 33, A/D converter 34, multiplexer 35 and writing into the frame memories 36R, 36G and 36B are generated from a timing generator 39. The above mentioned multiplexer 35 is switched as synchronized with the rotation of the above mentioned rotary filter 43 and the signals imaged under the field sequential light of R, G and B are written into the frame memories 36R, 36G and 36B corresponding to the respective colors.

The above mentioned frame memories 36R, 36G and 36B are simultaneously read out and the respective outputs are converted to analogue signals by the D/A converters 37, pass through a low-pass filters 38 and are output as R, G and B color signals to the monitor 7. The respective timings of reading out the above mentioned frame memories 36R, 36G and 36B and the D/A converter 37 are generated from a timing generator 40.

The object image is color-displayed in the above mentioned monitor 7.

Now, in this embodiment, a plurality of types of the electronic endoscope 1 are prepared and can be connected to the same video processor 6. Various types of electronic endoscopes can be used selectively in response to the observing objects. For example, an endoscope of a fine insertable part is used for the diseases of children and a stricture of the esophagus and a side viewing endoscope or high resolution endoscope will be used when a precise inspection is required. In such a case, it is necessary to use a small solid state imaging device for the endoscope of a fine insertable part and a large solid state imaging device of many pixels for the high resolution endoscope. However, in order to make the outside diameter of the insertable part as small as possible, it may be necessary to change the arranging manner between the small solid state imaging device and large solid state imaging device.

Figure 3:
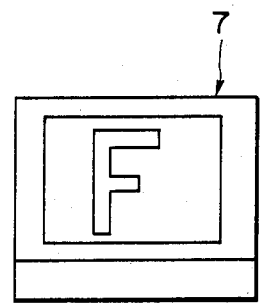
Figure 4:
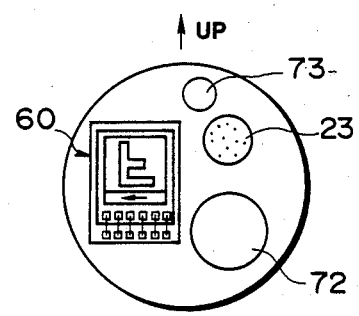
Figure 5:
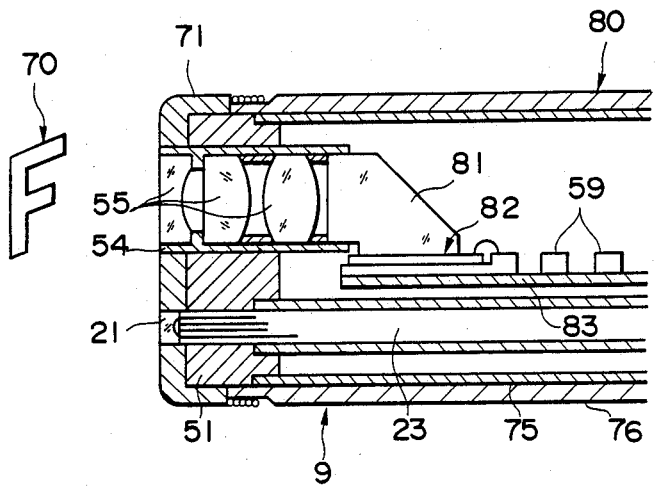
Figure 6:
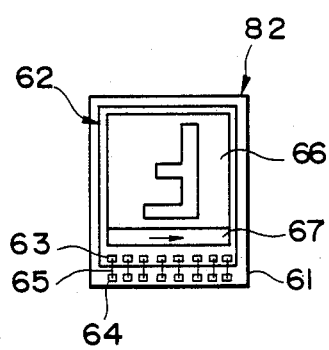
Figure 7:
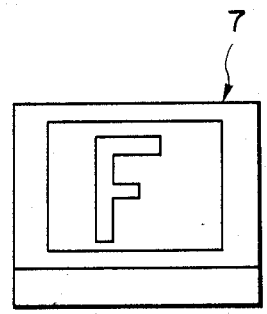
Figure 10:
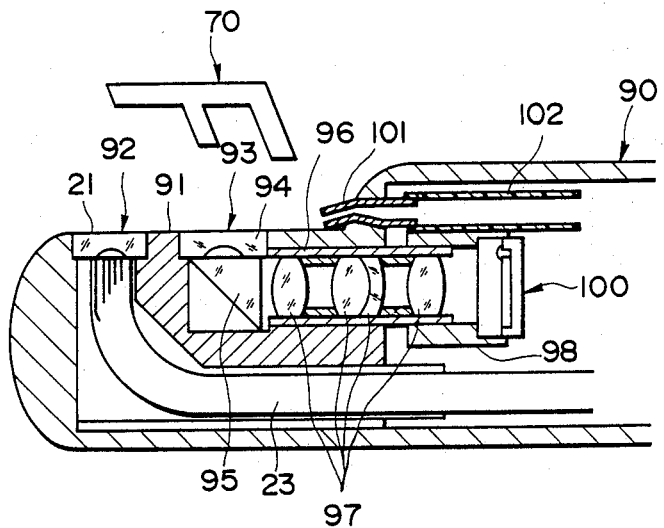
Figure 11:
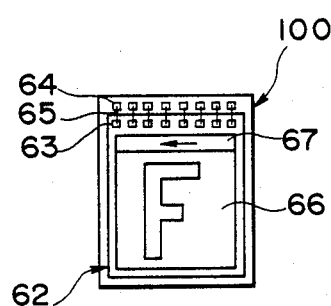
Figure 12:
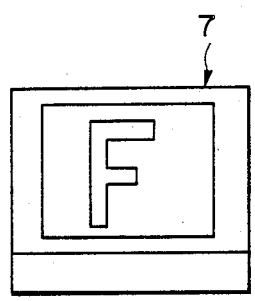

In the following, as examples of a plurality of types of endoscopes, a straight viewing endoscope using a small solid state imaging device is shown in FIGS. 1 to 4, a straight viewing endoscope using a large solid state imaging device is shown in FIGS. 5 to 7, a side viewing endoscope using a small solid state imaging device is shown in FIGS. 10 to 12 and a side viewing endoscope using a large solid state imaging device is shown in FIGS. 13 to 16.

Figure 1:
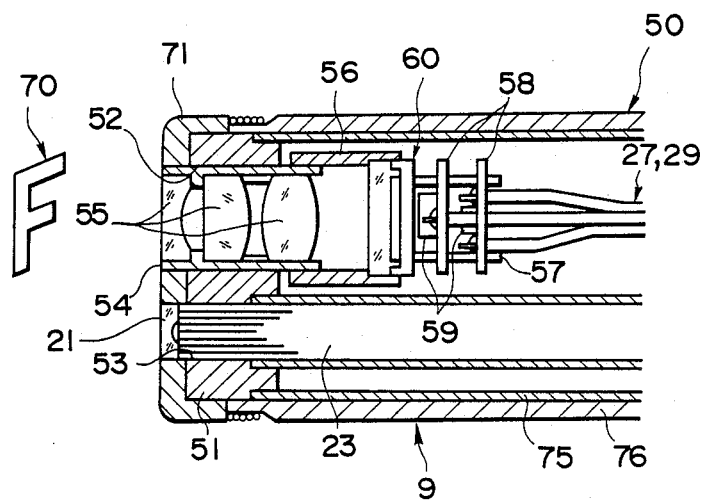
FIGS. 1 to 18 relate to the first embodiments of the present invention.

As shown in FIG. 1, the tip part 9 of a straight viewing endoscope 50 using a small solid state imaging device has a rigid columnar tip part body 51 and a cover member 71 externally fitted to the tip side of this tip part body 51. An observing through hole 52 and illuminating through hole 53 passing in parallel with the axial direction of the insertable part, a through hole forming a treating tool channel 72 and a through hole forming an air and water feeding channel 73 are formed in the tip part body 51 and cover member 71.

An objective lens system 55 held by an objective lens frame 54 is fitted in the above mentioned observing through hole 52. A device frame 56 is connected to the above mentioned objective lens 55 at the rear end and a solid state imaging device 60 arranged vertically to the axial direction of the insertable part is held by the above mentioned device frame 56 in the image forming position of the above mentioned objective lens system 54. In case the solid state imaging device 60 is small, the outside diameter of the tip part 9 can be made smaller by this arrangement. The leading foot 57 of the above mentioned solid state imaging device 60 is connected to a substrate 58 which is actually fitted with an electronic circuit 59 forming the pre-amplifier 28 and others. The signal lines 27 and 29 are connected to the above mentioned substrate 58.

On the other hand, the above mentioned illuminating through hole 53 is fitted on the tip side with a light distributing lens 21 and has on the rear end side of this light distributing lens 21 a light guide 23 inserted and fixed on the tip side.

A cylindrical tip cylinder 75 is connected to the above mentioned tip part body 51 at the rear end and contains and protects the above mentioned solid state imaging device 60 and others within it. Further, a tube 76 covering the above mentioned tip cylinder 75 and forming a sheath of the insertable part 2 is connected to the above mentioned tip part body 51 at the rear end.

Figure 2:
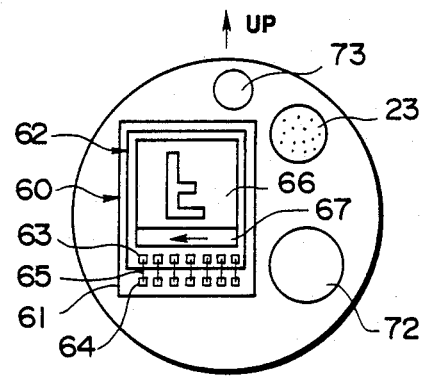

Now, for example, in a CCD, as shown in FIG. 2, the above mentioned solid state imaging device 60 has a rectangular package 61 and an imaging chip 62 die-bonded on this package 61 and an imaging chip 62 side bonding pad 63 and a package 61 side bonding pad 64 are connected with each other through bonding wires 65. The above mentioned imaging chip 62 has a light receiving part 66 and a horizontal transferring part 67. The above mentioned horizontal transferring part 67 and wire bonding parts are arranged downward of the picture image of the endoscope. The above mentioned imaging chip 62 and wire bonding parts are sealed with a glass or transparent resin.

The optical image of the object 70 is formed as an inverted image as shown in FIG. 2 on the light receiving part 66 of the above mentioned solid state imaging device 60. However, in FIG. 2, the formed image is represented as reflected and is therefore a back image (called also a mirror image). The signal charges accumulated in the above mentioned light receiving part 66 are transferred and read out in the direction indicated by the arrow (leftward in FIG. 2) by the above mentioned horizontal transferring part 67. The output signal of this solid state imaging device 60 is amplified by the pre-amplifier 28, is input into the video processor 6 through the signal line 29 and is processed to be a video signal by this video processor 6 without reversing the image and the video signal output from this video processor 6 is input into the monitor 7. In this monitor 7, as shown in FIG. 3, the object image is displayed as a right image and so that the upward direction of the endoscope may be upward of the monitor 7, that is, as an erect image.

The solid state imaging device 60 is not limited to be a CCD but may be any of such solid state imaging devices as a MOS type imaging device, CPD and SIT.

FIG. 4 shows an endoscope with a small diameter by using a smaller solid state imaging device 60 among straight viewing endoscopes using small solid state imaging devices. Even in this endoscope, the solid state imaging device 60 is arranged exactly the same as the solid state imaging device 60 in the endoscope shown in FIG. 2 and the direction of transferring the horizontal transferring part 67 is also the same.

The formation of the tip part of a straight viewing endoscope 80 using a large solid state imaging device shall be explained in the following:

As shown in FIG. 5, in this endoscope 80, a rectangular prism 81 is connected to an objective lens frame 54 at the rear end. A large solid state imaging device 82 arranged parallelly with the optical axis of an objective lens system 55, that is, parallelly with the axial direction of the insertable part is cemented to this rectangular prism 81 on the exit end surface. In case the large solid state imaging device 82 is used, the outside diameter of the tip part 9 can be made smaller by such an arrangement. The above mentioned solid state imaging device 82 is fixed on a substrate 83 which is actually fitted with the electronic circuit 59.

As shown in FIG. 6, the above mentioned solid state imaging device 82 is of substantially the same formation as of the small solid state imaging device 60 shown in FIG. 2 but is arranged in the same direction as the vertical direction of the formed object image and the transferring direction of the horizontal transferring part 67 is reverse to that of the solid state imaging device 60.

The other formations of the endoscope 80 are the same as of the straight viewing endoscope 50 using the small solid state imaging device shown in FIG. 1.

Figure 8:
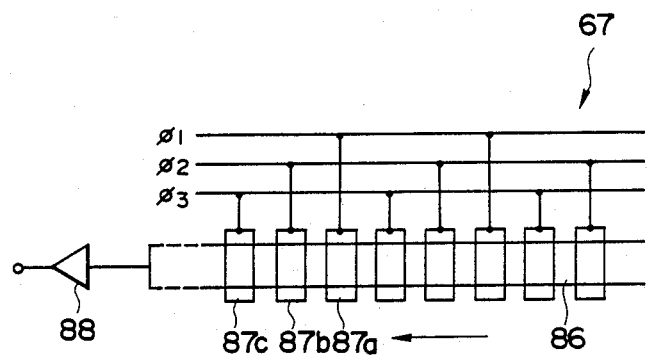
Figure 9:
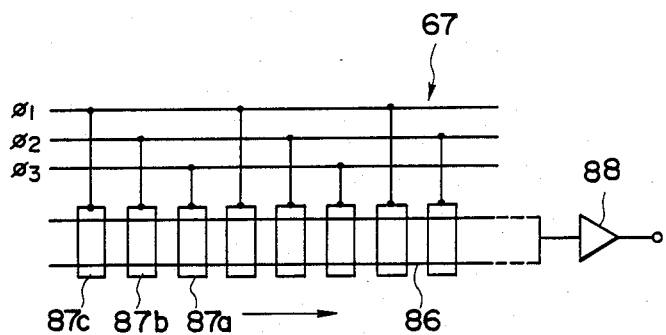

In the above mentioned endoscope 80, the object image formed on the solid state imaging device 82 by the objective lens system 55 and prism 81 is reflected once by the prism 81 and is therefore an image inverted with respect to the object image formed on the solid state imaging device 60 of the endoscope 50. That is to say, if the object image formed on the solid state imaging device 60 of the endoscope 50 is a right image, the object image formed on the solid state imaging device 82 of the endoscope 80 will be a mirror image (called also a back image). However, as described above, the directions in the vertical directions of the solid state imaging devices 60 and 82 with respect to the vertical direction of the formed object image are the same, the transferring direction of the horizontal transferring part 67 is reverse to that of the solid state imaging device 60, the image is processed to be a video signal by the video processor 6 without being inverted and, as shown in FIG. 7, the object image displayed in the monitor 7 is displayed as a right image the same as in the case of the above mentioned endoscope 50 and so that the upward direction of the endoscope may be upward of the monitor 7, An example of a means of reversing the transferring direction of the horizontal transferring part 67 in the case of using CCD's as the solid state imaging devices 60 and 82 shall be explained by using FIGS. 8 and 9. FIG. 8 shows the horizontal transferring part 67 of the solid state imaging device 60. FIG. 9 shows the horizontal transferring part 67 of the solid state imaging device 82. Either shows an example of a 3-phase driving CCD.

Three sets of gate electrodes 87a, 87b and 87c are repeatedly arranged sequentially in the transferring region 86 of the horizontal transferring part 67 of the solid state imaging device 60. 3-phase horizontal transferring pulses $\phi 1$, $\phi 2$ and $\phi 3$ are applied to the respective gate electrodes 87a, 87b and 87c. The signal charge is transferred to the left side in the drawing by these transferring pulses. A pre-amplifier 88 is provided in the output part on the left side of the above mentioned transferring region 86.

On the other hand, in the horizontal transferring part 67 of the solid state imaging device 82, the arrangement of the gate electrodes 87a, 87b and 87c is the same but the horizontal transferring pulses $\phi 1$, $\phi 2$ and $\phi 3$ are applied to the respective gate electrodes in the order quite reverse to the case of the above mentioned solid state imaging device 60. That is to say, the horizontal transferring pulse $\phi 3$ is applied to the gate electrode 87a, the horizontal transferring pulse $\phi 2$ is applied to the gate electrode 87b and the horizontal transferring pulse $\phi 1$ is applied to the gate electrode 87c. Therefore, the signal charge is transferred to the right side in the drawing. Also, a pre-amplifier 88 is provided in the output part on the right side of the above mentioned transferring region 86.

The CCD may be made to select the reading out direction by the manner of winding so that, in the case of incorporating this CCD into the endoscope, the reading out direction may be selected by the winding or the like.

Even in the case of the straight viewing endoscope using the large solid state imaging device, further the solid state imaging device is large or small. However, in either case, the solid state imaging device is arranged just the same as the above mentioned solid state imaging device 80 and the transferring direction is also made the same.

The signal can be easily processed by the common video processor 6 for CCD's of different numbers of pixels by using a frame memory and driving frequency corresponding to the CCD of the maximum number of pixels. This is mentioned, for example, in the specification of a U.S. Pat. No. 4,746,975 to the present applicant.

The formation of the tip part of the side viewing endoscope 90 using the small solid state imaging device shall be explained in the following.

As shown in FIG. 10, a plane part parallel with the axial direction of the insertable part is formed in one side part of the tip part body 91 and an illuminating window 92 and observing window 93 are formed in the order from the tip side on this plane part. The above mentioned illuminating window 92 is fitted with a light distributing lens 21. A light guide 23 is connected to this light distributing lens 21 on the rear end side, is bent on the tip side to the above mentioned light distributing lens 21 side and is opposed to the above mentioned light distributing lens 21. The above mentioned observing window 93 is fitted with a cover lens 94 forming an objective lens system. A rectangular prism 95 reflecting rearward in the axial direction of the insertable part the light having passed through this cover lens 94 is arranged inside this cover lens 94. A lens system 97 forming the objective lens system and held by a lens frame 96 is arranged in the rear of the exit end surface of this rectangular prism 95. A device frame 98 is connected to the above mentioned lens frame 96 in the rear end part. A solid state imaging device 100 arranged vertically to the axial direction of the insertable part is held by the above mentioned device frame 98 in the image forming position of the above mentioned objective lens system.

As shown in FIG. 11, the above mentioned solid state imaging device 100 is of substantially the same formation as of the small solid state imaging device 60 shown in FIG. 2 but is arranged in the same direction with repect to the vertical direction of the formed object image and the transferring direction of the horizontal transferring part 67 is reverse to that of the solid state imaging device 60. That is to say, the transferring direction of the horizontal transferring part 67 of the solid state imaging device 100 is the same as of the solid state imaging device 82.

An air and water feeding nozzle 101 is arranged in the rear of the above mentioned observing window 93 and is connected with an air and water feeding tube 102 forming an air and water feeding channel.

In the above mentioned endoscope 90, the object image formed on the solid state imaging device 82 by the objective lens system including the rectangular prism 95 has been once reflected by the rectangular prism 95 and therefore, as shown in FIG. 11, is an image inverted with respect to the object image formed on the solid state imaging device 60 of the straight viewing endoscope 50. However, as described above, as the transferring direction of the horizontal transferring part 67 is made reverse to that of the solid state imaging device 60, the image is processed to be a video signal by the video processor 6 without being inverted and, as shown in FIG. 12, the object image displayed in the monitor 7 is displayed as a right image the same as in the case of the straight viewing endoscopes 50 and 80 and so that the upward direction of the endoscope may be upward of the monitor 7.

If a dach prism is used instead of the above mentioned rectangular prism 95, this prism is more or less larger but the transferring direction of the horizontal transferring part 67 of the solid state imaging device 100 can be made the same as of the solid state imaging device 60 of the straight viewing endoscope 50 using the small solid state imaging device and the solid state imaging device can be made common to the straight viewing endoscope 50.

Figure 13:
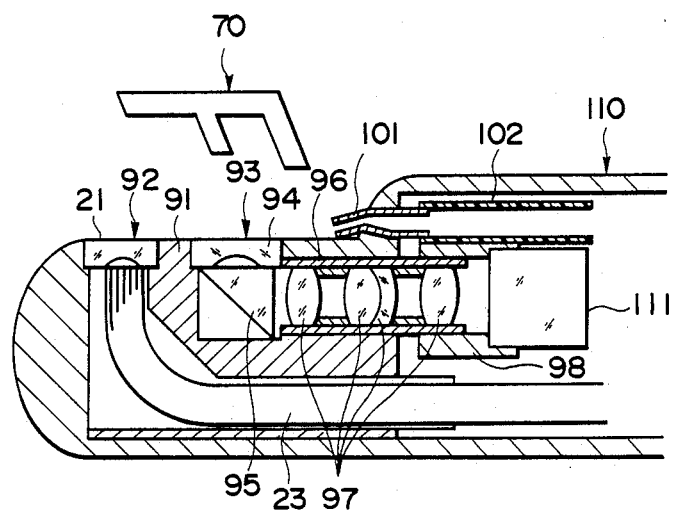
Figure 14:
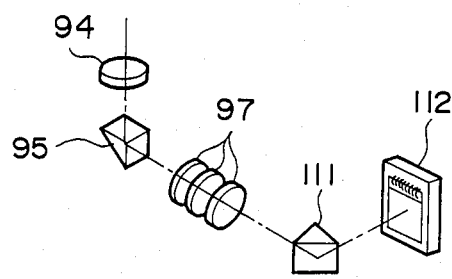

The formation of the tip part of a side viewing endoscope 110 using a large solid state imaging device shall be explained in the following:

As shown in FIG. 13, in this endoscope 110, a rectangular prism 111 is fitted to a device frame 98 and, as shown in FIG. 14, a large solid state imaging device 112 arranged in parallel with the axial direction of the insertable part is provided as opposed to the exit end surface of the above mentioned rectangular prism 111. In case the large solid state imaging device 112 is used, the outside diameter of the tip part can be made smaller by such an arrangement.

Figure 15:
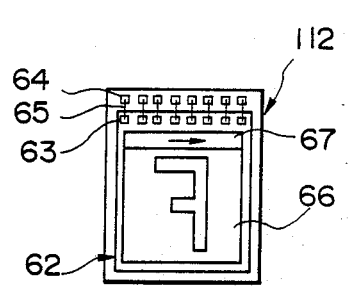

As shown in FIG. 15, the above mentioned solid state imaging device 112 is of substantially the same formation as of the small solid state imaging device 100 shown in FIG. 11 but is arranged in the same direction with respect to the vertical direction of the formed object image and the transferring direction of the horizontal transferring part 67 reverse to that of the solid state imaging device 100.

The other formations of the endoscope 110 are the same as of the side viewing endoscope 90 using the small solid state imaging device shown in FIG. 10.

Figure 16:
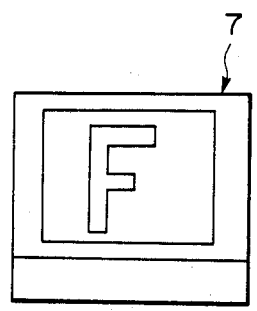

In the above mentioned endoscope 110, the image is reflected twice by the rectangular prisms 95 and 111 and therefore, as shown in FIG. 15, the image formed on the solid state imaging device 112 is an image inverted with respect to the object image formed on the solid state imaging device 100 of the endoscope 90. However, as described above, the solid state imaging device 112 is arranged in the same direction as of the solid state imaging device 100 with respect to the vertical direction of the formed object image and the transferring direction of the vertical transferring part 67 is made reverse to that of the solid state imaging device 100, therefore the image is processed to be a video signal by the video processor 6 without being inverted and, as shown in FIG. 16, the object image displayed in the monitor 7 is displayed as a right image the same as in the case of the above mentioned endoscope 90 and so that the upward direction of the endoscope may be upward of the monitor 7.

The same as in the case of the above mentioned endoscope 90, if a dach prism is used instead of the above mentioned rectangular prism 95, the transferring direction of the horizontal transferring part 67 of the solid state imaging device 112 can be made the same as of the solid state imaging device 82 of the straight viewing endoscope 80 and the solid state imaging device can be made common to the straight viewing endoscope 80.

Even in the side viewing endoscopes 90 and 110, in the respective small solid state imaging device 100 and large solid state imaging device 112, further the solid state imaging devices may be large and small. However, in either case, the solid state imaging devices are unified in the arrangement and the transferring direction of the horizontal transferring part 67.

As explained above, in this embodiment, in the four types of endoscopes of the straight viewing endoscopes 50 and 80 and side viewing endoscopes 90 and 110, the direction of the solid state imaging device is unified with respect to the vertical direction of the object image, the front and back of the observed image are unified by changing the transferring direction of the horizontal transferring part of the solid state imaging device, that is to say, the observed image is unified to be either right image or mirror image and the direction of the observed image, that is, the position of the rotating direction is unified.

Therefore, without making a process of unifying such front, back and direction of the observed image as the image inversion on the side of the video processor 6 used in common with the above mentioned four types of endoscopes 50, 80, 90 and 110, in the case of using any of the endoscopes 50, 80, 90 and 110, the object image is displayed as a right image and so that the upward direction of the endoscope may be upward of the monitor 7.

Thus, according to this embodiment, a plurality of kinds of endoscopes can be used by the common video processor 6, such front, back and direction of the observed image as the image inversion need not be processed to be unified on the video processor 6 side and therefore this video processor 6 does not require such circuits as a discriminating circuit discriminating the type of the endoscope, an image inverting circuit and a switching circuit switching the circuit in response to the kind of the endoscope and can be made simple in formation, small in size and low in cost. Also, the endoscope side does not require a means of discriminating the type of endoscope and can be made simple in formation and low in cost.

Figure 19:
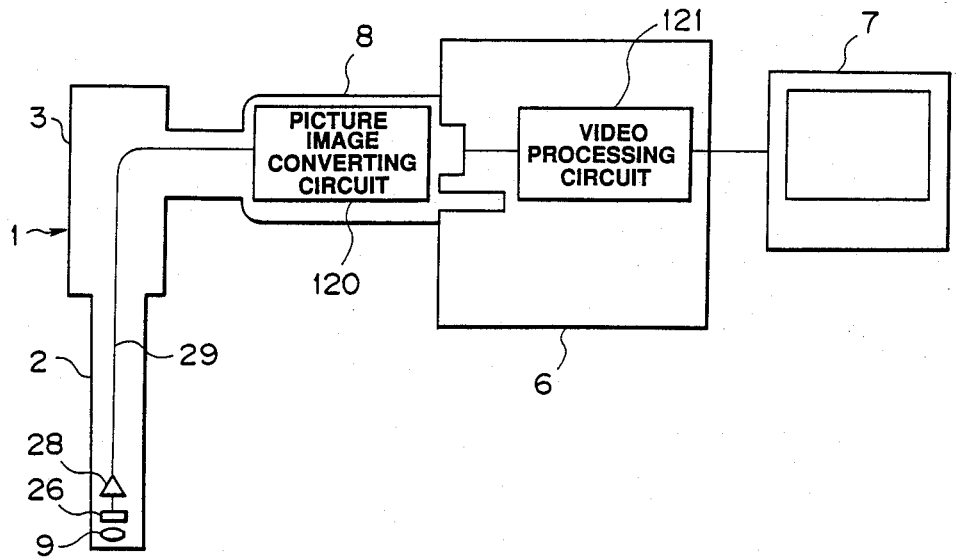
FIG. 19 is an explanatory view showing the scheme of an endoscope system.
Figure 20:
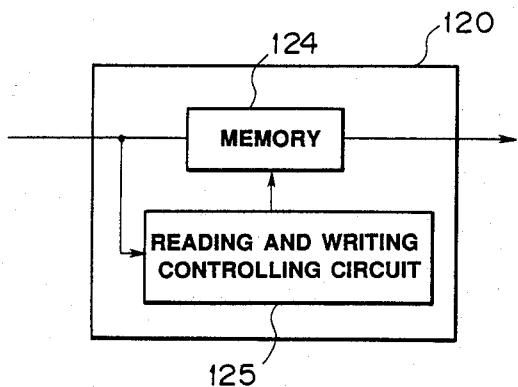
FIG. 20 is a block diagram showing a picture image converting circuit.
Figure 21:
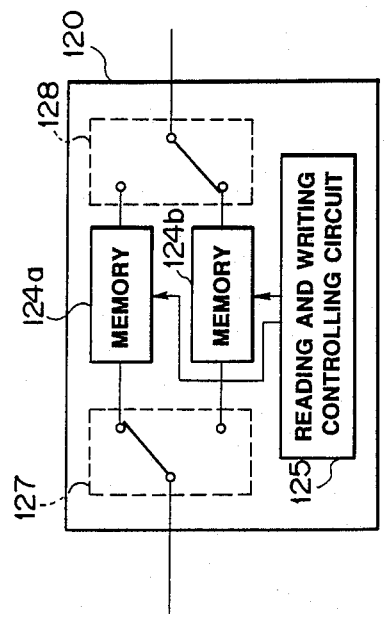
FIG. 21 is a block diagram showing a picture image converting circuuit in a modification of this embodiment.
Figure 22:
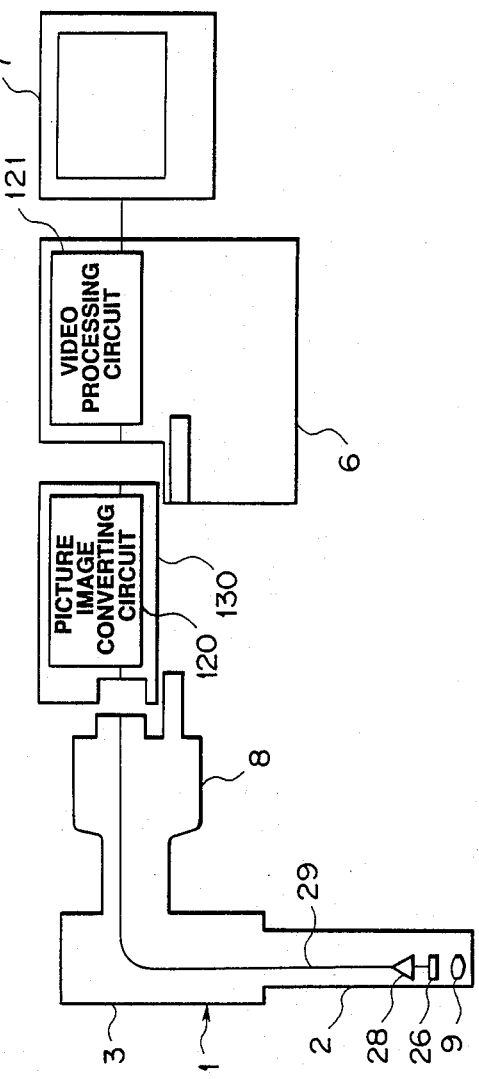
FIG. 22 is an explanatory view showing the scheme of an endoscope system of the third embodiment of the present invention.

The second embodiment of the present invention is shown in FIGS. 19 to 21.

In this embodiment, a picture image converting circuit 120 is provided within a connector of an electronic endoscope 1 connected to a video processor 6. A signal line 29 transmitting the output signal of a solid state imaging device 26 of the above mentioned electronic endoscope 1 is connected to a video processing circuit 121 within the video processor 6 through the above mentioned image converting circuit 120. The above mentioned video processing circuit 121 is of the same formation except the light source apparatus 25 as of the video processor 6 in FIG. 18.

As shown in FIG. 20, the above mentioned picture image converting circuit 120 has a memory 124 storing the output signal of the above mentioned solid state imaging device 26 and a reading and writing controlling circuit 125 controlling writing into and reading out of this memory 124. The above mentioned reading and writing controlling circuit 125 can change the order of writing into and reading out of the above mentioned memory 124 and controls the timing of reading out after writing in ends in response to the signal from the above mentioned solid state imaging device 26.

In this embodiment, by changing the order of writing into and reading out of the memory 124 by the above mentioned reading and writing controlling circuit 125, even if the picture image from the solid state imaging device 26 is a back image or an inverted image or is rotated by 90°, it can be converted to a picture image in a predetermined direction. For example, for the time of writing in, by reversing the scanning direction at the time of reading out, the back image can be converted to a right image. For the time of writing in, by reversing the order of the scanning direction and scanning line at the time of reading out, the inverted image can be converted to an erect image. For the time of writing in, by rotating by 90° the scanning direction at the time of reading out, the picture image can be rotated by 90°. Therefore, whatever the picture image from the solid state imaging device 26 may be, by the above mentioned picture image converting circuit 120, the front picture image, back picture image and direction of the picture image can be unified and the video processing circuit 121 can be used in common with various type of endoscopes.

Also, as shown in FIG. 21, the above mentioned picture image converting circuit 120 may be provided with two memories 124a and 124b. Switches 127 and 128 and the memories 124a and 124b are controlled so that the signal from the solid state imaging device 26 may be input alternately into one of the memories 124a and 124b by the switching switch 127, may be written into this one memory, may be simultaneously read out of the other memory and may be output through the switching switch 128. Thus, even the case of an image operating at a high speed can be coped with.

According to this embodiment, even in the case that the type of the solid state imaging device 26, layout and optical system are limited and the direction of a picture image can not be made a desired direction in the output stage of the solid state imaging device 26, the direction of the picture image input into the video processor 6 can be unified.

The other formations, operations and effects are the same as in the first embodiment.

In a third embodiment, between the connector 8 of the electronic endoscope 1 and the video processor 6, an adapter 130 connecting both is provided and the picture image converting circuit 120 in the second embodiment is provided within this adapter 130.

Various kinds of the above mentioned adapter 130 are prepared in response to the types of the endoscopes to convert the back image to a right image, to convert the inverted image to an erect image and to rotate the picture image. The adapter 130 corresponding to the endoscope to be used is fitted in advance or the adapter 130 is fitted in advance to the connector 8 of the endoscope as required.

According to this embodiment, the endoscope is not required to be provided with the picture image converting circuit 120 and therefore can be made compact. Needless to say, the video processor 6 is not required to discriminate the type of the endoscope and to switch the circuit, therefore is compact, is cheap and is high in reliability.

The other formations, operations and effects are the same as in the second embodiment.

Figure 23:
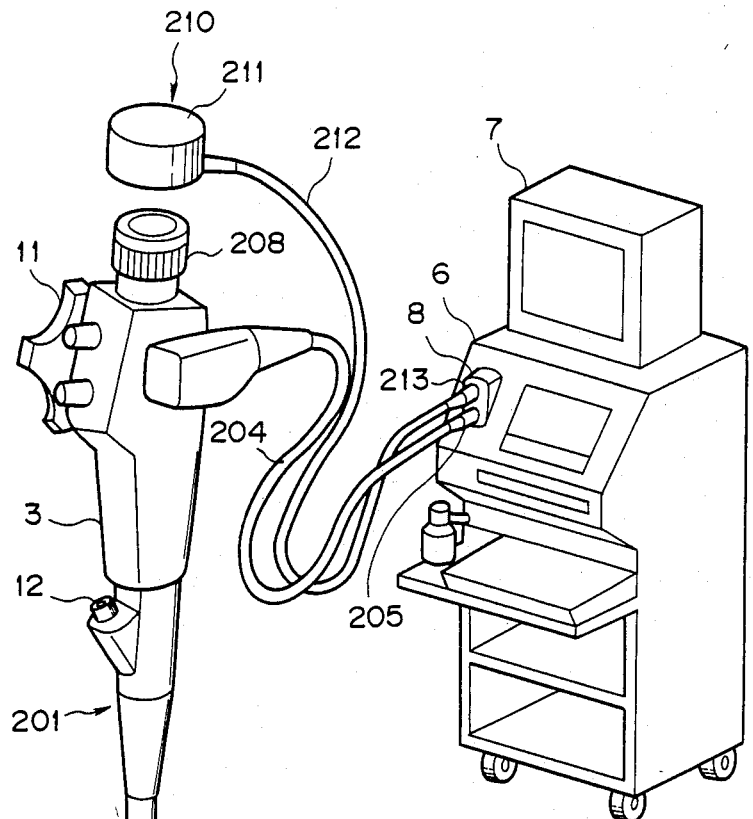
FIGS. 23 and 24 relate to the fourth embodiment of the present invention.
Figure 24:
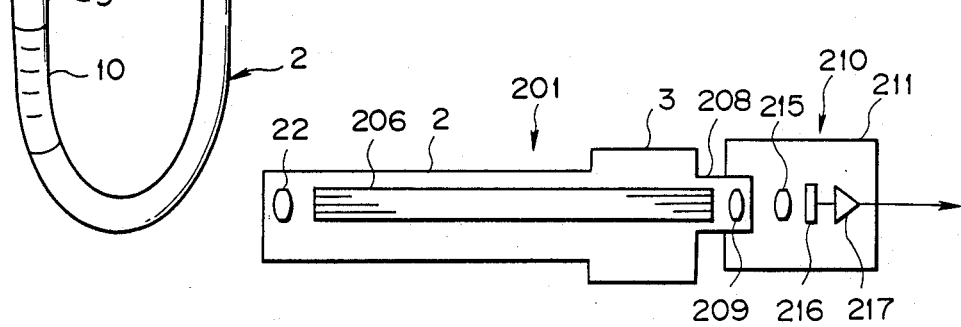

The fourth embodiment of the present invention is shown in FIGS. 23 and 24.

In this embodiment, as shown in FIG. 23, the endoscope apparatus is provided with a fiber scope 201 instead of the electronic endoscope 1 and a video converter 210 which is a television camera removably fitted to the eyepiece part 208 of this fiber scope 201.

The above mentioned fiber scope 201 is provided with an elongate and, for example, flexible insertable part 2 and a thick operating part 3 connected to this insertable part 2 at the rear end. A flexible light guide cable 204 is extended sidewise from the above mentioned operating part 3 and is provided at the end with a light guide connector 205 connected to a connector receptacle 8 of a video processor 6.

The above mentioned insertable part 2 is provided on the tip side with a tip part 9 and curvable part 10. The operating part 3 is provided with a curving operation knob 11 operating to curve the above mentioned curvable part 10.

The above mentioned operating part 3 is provided with a treating tool inserting port 12 communicating with a treating tool channel provided within the above mentioned insertable part 2 and is provided at the rear end with the above mentioned eyepiece part 208.

As shown in FIG. 24, the above mentioned tip part 9 is provided with an image forming optical system 22. The tip surface of an image guide 206 made of a fiber bundle is arranged in the image forming position of this image forming optical system 22. This image guide 206 is inserted through the insertable part 2, is extended in the rear end part to the above mentioned eyepiece part 208 and is opposed on the rear end surface to an eyepiece lens 209 within the eyepiece part 208. The object image formed by the above mentioned image forming optical system 22 is led to the eyepiece part 208 by the image guide 206 and can be observed from this eyepiece part 208.

A video converter 210 fitted to the above mentioned eyepiece part 208 has a body 211. A cable 212 is extended from this body 211 and is provided at the end with a connector 213 connected to the connector receptacle 8 of the video processor 6. A solid state imaging device 216 such as a CCD, an image forming lens 215 forming an image of the light from the above mentioned eyepiece part 208 on the above mentioned solid state imaging device 216 and a pre-amplifier 217 amplifying the output signal of the above mentioned solid state imaging device 216 are provided within the above mentioned body 211. The output signal of the above mentioned pre-amplifier 217 is input into the video processor 6 through the above mentioned cable 212 and connector 213.

The picture image input into the video processor 6 from the above mentioned video converter 210 is uified to be a image front, or back image and is unified in direction by such means as are shown in the first to third embodiments.

The above mentioned video processor 6 is the same as is shown in the first embodiment and is used in common with a plurality of types of endoscope apparatuses.

The other formations, operations and effects are the same as in the first embodiment.

The present invention is not limited to the above mentioned embodiments. For example, the types of the endoscopes are not limited to the four types in the first embodiment but may include an oblique viewing type. In any kind of endoscope, in the objective optical system of the same number of reflections (or inversions) of the image or an odd number or even number of reflections (or inversions) of the image, the direction of the solid state imaging device with respect to the vertical direction of the object image to be formed is unified, the transferring direction of the horizontal transferring part of the solid state imaging device is arranged in the same direction and, in an odd number and even number of reflections (or inversions) of the image, by reversing the transferring direction of the horizontal transferring part, the front image, or back image and the direction of the endoscope image are unified.

The plurality of types of endoscope apparatuses may be all electronic endoscopes such as in the first embodiment, may be all fiber scopes and video converters such as in the fourth embodiment or may include both of them.

Also, the front and back of the image may be unified by an optical means such as a lens, prism or mirror.

The color imaging system is not limited to be of a field sequential type but may be of a simultaneous type.

The manner of unifying the image is not limited to unify a right image but a back image may be unified and the back image may be always converted to a right image on the signal processing apparatus side.

As explained above, according to the present invention, there is an effect that, as the front or back of an observed image is unified on the side of a plurality of types of endoscopes, with a simple formation, without inverting the image, a common signal processing apparatus can be used for a plurality of types of endoscopes.

It is apparent that, in this invention, working modes different in a wide range can be formed on the basis of this invention without deviating from the spirit and scope of the invention. This invention is not restricted by its specific working modes except being limited by the appended claims.

What is claimed is:

1. An endoscope system in which the displayed image is unified comprising:
   a plurality of types of endoscope apparatuses, each having an elongate insertable part, an image forming optical system provided in a tip part of said insertable part and an imaging means imaging an object image formed by said image forming optical system, at least one type of said plurality of types of endoscope apparatuses being different from the other types in respect to whether the object image formed by said image forming system is a right image or a mirror image;
   a signal processing apparatus, used in common with said plurality of types of endoscope apparatuses, said signal processing apparatus using a same process in response to the type of the endoscope apparatus with respect to an inversion between the right image and the mirror image and said signal processing apparatus processing an output signal of said imaging means of each endoscope apparatus to be a video signal; and
   a first unifying means for unifying the picture image in the signal output from said plurality of endoscopes to be the right image or the mirror image and for inputting the unified picture image into said signal processing apparatus, said first unifying means formed as counterparts to each of said endoscope apparatuses to unify the picture image in the signal output by the endoscope apparatuses and the first unifying means.

2. An endoscope system according to claim 1 wherein said plurality of types of endoscope apparatuses are further provided with a second unifying means for unifying a position of a rotating direction of the picture image in the output signal of said imaging means for all the endoscope apparatuses, said output signal input to said signal processing apparatus, said second unifying means formed as counterparts to each of said endoscope apparatuses.

3. An endoscope system according to claim 1 or 2 wherein said first unifying means has a means of making a scanning direction different among said plurality of kinds of endoscope apparatuses when reading out the signal of said imaging means.

4. An endoscope system according to claim 1 or 2 wherein said imaging means has a solid state imaging device and said first unifying means has a means of making a transferring direction of the horizontal transferring part of said solid state imaging device different among said plurality of types of endoscope apparatuses.

5. An endoscope system according to claim 2 wherein said imaging means has a solid state imaging device and, when the position of the rotating direction of the image formed by said image forming optical system is different depending on said image forming optical system, said second unifying means has a means of arranging in the same direction among said plurality of types of endoscopes said solid state imaging device with respect to a vertical direction of the image formed by said image forming optical system.

6. An endoscope system according to claim 1 or 2 wherein said first unifying means has a memory means for storing the signals from said imaging means and a memory controlling means which can change the order of writing the signal into said memory means and the order of reading the signal out of said memory means.

7. An endoscope system according to claim 6 wherein said memory means and memory controlling means are provided within a connector of said endoscope apparatus connected to said signal processing apparatus.

8. An endoscope system according to claim 6 wherein further including an adapter connecting said endoscope apparatus and said signal processing apparatus with each other and said memory means and memory controlling means are provided within said adapter.

9. An endoscope system according to claim 2 wherein said first unifying means and said second unifying means have as forming both means a memory means storing the signal from said imaging means and a memory controlling means which can change the order of writing the signal into said memory means and the order of reading the signal out of said memory means.

10. An endoscope system according to claim 9 wherein said memory means and memory controlling means are provided within a connector of the endoscope apparatus connected to said signal processing apparatus.

11. An endoscope system according to claim 9 wherein further including an adapter connecting said endoscope apparatus and said signal processing apparatus with each other, and said memory means and memory controlling means are provided within said adapter.

12. An endoscope system according to claim 1 or 2 wherein, in at least one type of said plurality of types of endoscopes, said imaging means has a solid state imaging device arranged in the image forming position of said image forming optical system within the tip part of said insertable part.

13. An endoscope system according to claim 1 or 2 wherein at least one type of said plurality of types of endoscope apparatus is further provided with an eyepiece part provided on the rear end side of said insertable part and an image transmitting means transmitting the object image formed by said image forming optical system to said eyepiece part.

14. An endoscope system in which the displayed picture image is unified comprising:
   a plurality of types of endoscope apparatuses each having an elongate insertable part, an imaging forming optical system provided in a tip part of said insertable part and an imaging means using a solid state imaging device imaging an object image formed by said image forming optical system, at least one type of said plurality of types of endoscope apparatuses being different from the other types in size of said solid state imaging device;
   a signal processing apparatus, used in common with said plurality of types of endoscope apparatuses, said signal processing apparatus using a same process in response to the type of endoscope apparatus with respect to an inversion between a right image and a mirror image and said signal processing apparatus processing an output signal of said imaging means of each endoscope apparatus to be a video signal; and
   a first unifying means for unifying a picture image in the signal output from said plurality of endoscopes to be a right image or a mirror image and said first unifying means for inputting the picture image into said signal processing apparatus, said first unifying means formed as counterparts to each of said endoscope apparatuses to unify the picture image in the signal output from the endoscope apparatus and first unifying means.

15. In an endoscope apparatus comprising a plurality of types of endoscope apparatuses each having an elongate insertable part, an image forming optical system provided in a tip part of said insertable part and an imaging means imaging the object image formed by said image forming optical system, including at least one type of endoscope being a different type in which said image formed by said image forming optical system is a right image or mirror image, and a signal processing apparatus processing an output signal of said imaging means of each endoscope apparatus to be a video signal, a method of unifying the picture image in the signal output from said signal processing means to be a right image or mirror image including unifying the picture image in the signal output from said plurality of types of endoscope apparatus with a unifying means to be a right image or a mirror image before said picture image is input into said signal processing apparatus, said unifying means formed as counterparts to each of said endoscope apparatuses.

16. In an endoscope system comprising a plurality of types of endoscope apparatuses each having an elongate insertable part, an image forming optical system provided in a tip part of said insertable part and an imaging means imaging an object image formed by said image forming optical system, including at least one type of endoscope apparatus in which the image formed by said image forming optical system is different from the other types of endoscope apparatuses with respect to whether the image is a right image or a mirror image, and a signal processing apparatus processing an output signal of said imaging means of each endoscope apparatus to be a video signal, a method for unifying a picture image in the signal output from said plurality of types of endoscope apparatuses and input into said signal processing apparatus to be a right image or a mirror image including making a scanning direction different when reading out the signal of said imaging means from said endoscope apparatus which is different from said other types of endoscope apparatuses.

17. A method according to claim 16 wherein said imaging means has a solid state imaging device and a transferring direction of a horizontal transferring part of said solid state imaging device is different from said plurality of types of endoscope apparatuses in order to unify the picture image to be a right image or a mirror image.

18. In an endoscope system comprising a plurality of types of endoscope apparatuses, each having an elongate insertable part, an image forming optical system provided in a tip part of said insertable part and an imaging means imaging an object image formed by said image forming optical system, including at least one type of endoscope apparatus in which the image formed by said image forming optical system is different from the other types of endoscope apparatuses with respect to whether the image is a right image or a mirror image, a signal processing apparatus processing an output signal of said imaging means of each endoscope apparatus to be a video signal, a method of unifying a picture image in the signal output from said plurality of types of endoscope apparatuses and input into said signal processing apparatus to be a right image or a mirror image and unifying a position of a rotating direction including the steps of:
   making a transferring direction of a horizontal transferring part of said solid state imaging device different from said plurality of types of endoscope apparatuses in order to unify the picture image to be the right image or the mirror image; and
   arranging said solid state imaging device in a same direction with respect to a vertical direction of the image formed by said image forming optical system in order to unify a position of the rotating direction of the picture image.

19. An endoscope system according to claim 1 wherein said first unifying means is integrated into an inside of said endoscope apparatuses.

20. An endoscope system according to claim 2 wherein said second unifying means is integrated into an inside of said endoscope apparatuses.

21. An endoscope system in which a displayed image is unified comprising:
   a plurality of types of endoscope apparatuses, each having an elongated insertable part, an image forming optical system provided in a tip part of said insertable part and an imaging means using a solid state imaging device imaging an object image formed by said image forming optical system, at least one type of said plurality of types of endoscope apparatuses being different from the other types in size of said solid state imaging device;
   a signal processing apparatus used in common with said plurality of types of endoscope apparatuses, said signal processing apparatus having a same process in response to the type of the endoscope apparatus with respect to a positional alignment of a rotating direction of the picture image, and said signal processing apparatus processing the output signal of said imaging means of each endoscope apparatus to be a video signal; and unifying means for unifying the position of the rotating direction of the picture image in the signal output from said plurality of endoscopes and input into said signal processing apparatus, said unifying means formed as counterparts to each of said endoscope apparatuses to unify the rotating direction of the picture image in the signal output from said endoscope apparatus and said unifying means.

* * * * *